US012655087B2

(12) United States Patent
Lee et al.

(10) Patent No.: US 12,655,087 B2

(45) Date of Patent: Jun. 16, 2026

(54) APPARATUS AND METHOD OF PRODUCING DIMETHYL CARBONATE BY REACTIVE DISTILLATION USING HYBRID HEAT INTEGRATION

(71) Applicant: KOREA ADVANCED INSTITUTE OF SCIENCE AND TECHNOLOGY, Daejeon (KR)

(72) Inventors: Jae Woo Lee, Daejeon (KR); Minyong Lee, Daejeon (KR)

( * ) Notice: Subject to any disclaimer, the term of this patent is extended or adjusted under 35 U.S.C. 154(b) by 518 days.

(21) Appl. No.: 18/312,763

(22) Filed: May 5, 2023

(65) Prior Publication Data

US 2023/0365486 A1 Nov. 16, 2023

(30) Foreign Application Priority Data

May 10, 2022 (KR) ......................... 10-2022-0057281

(51) Int. Cl.

| | |
|---|---|
| *B01D 1/28* | (2006.01) |
| *B01D 3/00* | (2006.01) |
| *B01D 3/14* | (2006.01) |
| *C07C 68/065* | (2020.01) |
| *C07C 68/08* | (2006.01) |

(52) U.S. Cl.

CPC .............. *C07C 68/065* (2013.01); *B01D 1/28* (2013.01); *B01D 3/007* (2013.01); *B01D 3/009* (2013.01); *B01D 3/143* (2013.01); *C07C 68/08* (2013.01)

(58) Field of Classification Search

CPC .......... B01D 1/28; B01D 3/007; B01D 3/009; B01D 3/143; C07C 68/065; C07C 68/08

See application file for complete search history.

(56) References Cited

U.S. PATENT DOCUMENTS 6,295,840 B1 * 10/2001 Smith .................. F25J 3/04303
62/648
7,141,641 B2 * 11/2006 Murthy .................. B01D 3/009
203/64

(Continued)

FOREIGN PATENT DOCUMENTS

CN 103626656 A * 3/2014 .......... C07C 269/08
KR 1020190089192 A 7/2019

(Continued)

OTHER PUBLICATIONS

Huang, Z., et al., "Novel Procedure for the Synthesis of Dimethyl Carbonate by Reactive Distillation", Ind. Eng. Chem. Res., 2014, pp. 3321-3328, vol. 53, Publisher: ASC Publications.

(Continued)

*Primary Examiner* — Jonathan Miller

(57) ABSTRACT

Disclosed is a distillation apparatus having a various heat exchange methods added to a process of producing dimethyl carbonate using reactive distillation and pressure-swing distillation. According to the disclosure, internal and external heat integration between a high-pressure and a low-pressure distillation column, which constitute pressure-swing distillation columns, is applied to a dimethyl carbonate production process, and a vapor recompression heat pump configured to compress and heat a fluid and transfer the heat to a fluid having a relatively low temperature is applied to achieve additional heat exchange with a reactive distillation column, thereby improving the dimethyl carbonate production process in terms of energy and economic efficiency by reducing energy consumption while reducing investment and operating costs of a reboiler and a condenser, which are required in a conventional process.

14 Claims, 5 Drawing Sheets

(56) References Cited

U.S. PATENT DOCUMENTS

| | | | | |
|---|---|---|---|---|
| 7,288,668 B2 * | 10/2007 | Ryu | .......................... | C07C 68/08 |
| | | | | 558/274 |
| 2007/0112214 A1 * | 5/2007 | Ryu | .......................... | C07C 68/08 |
| | | | | 558/274 |
| 2020/0071255 A1 * | 3/2020 | Anapat | .................... | C07C 68/08 |

FOREIGN PATENT DOCUMENTS

| | | | | |
|---|---|---|---|---|
| KR | 1020200096981 A | 8/2020 | | |
| WO | WO-2014001855 A1 * | 1/2014 | ............. | C07C 68/08 |
| WO | WO-2016151508 A1 * | 9/2016 | ............. | C07C 68/08 |

OTHER PUBLICATIONS

Knapp, J.P., et al., "A New Pressure-Swing-Distillation Process for Separating Homogeneous Azeotropic Mixtures", Ind. Eng. Chem. Res., 1992, pp. 346-357, vol. 31, Publisher: American Chemical Society.

Lee, J.W., et al., "Circumventing an Azeotrope in Reactive Distillation", Ind. Eng. Chem. Res., 2000, pp. 1061-1063, vol. 39, Publisher: American Chemical Society.

Lee, H., et al., "CFD-aided design of internally heat-integrated pressure-swing distillation for ternary azeotropic separaton constrained by pinch pressure", Applied Thermal Engineering, 2021, 117198, vol. 195, Publisher: Elsevier.

Lee, M., et al., "Enhanced energy efficiency and reduced CO2 emissions by hybrid heat integration in dimethyl carbonate production systems", Separation and Purification Technology, 2022, 120598; https://doi.org/10.1016/j.seppur.2022.120598, vol. 287, Publisher: Elsevier.

Mujumdar, S., et al., "Mg—MoF-74/Polyvinyl acetate (PVAc) mixed matrix membranes for CO2 separation", Separation and Purification Technology, 2019, doi:https://doi.org/10.1016/j.seppur.2019116411.

Wang, S-J, et al., "Plant-wide design and control of DMC synthesis process via reactive distillation and thermally coupled extractive distillation", Computers and Chemical Engineering, 2010, pp. 361-373, vol. 34, Publisher: Elsevier.

* cited by examiner

APPARATUS AND METHOD OF PRODUCING DIMETHYL CARBONATE BY REACTIVE DISTILLATION USING HYBRID HEAT INTEGRATION

CROSS-REFERENCE TO RELATED APPLICATION

This application claims priority to and the benefit under 35 USC § 119 of Korean Patent Application No. 10-2022-0057281 filed in the Korean Intellectual Property Office on May 10, 2022, the entire contents of which are incorporated herein by reference, for all purposes.

BACKGROUND OF THE INVENTION

1. Field of the Invention

The present invention relates to a distillation apparatus and method having a heat exchange function added to a process of producing dimethyl carbonate using reactive distillation and pressure-swing distillation, and more particularly, to a dimethyl carbonate production process improved in terms of energy and economic efficiency as a result of applying internal and external heat integration between pressure-swing distillation columns and applying a vapor recompression heat pump to achieve additional heat exchange through heat integration with a reactive distillation column.

2. Description of the Related Art

In an azeotrope, when a solution composed of two liquid phase components is boiled, the proportions of components in the liquid and the gas become the same. During distillation, the proportions of components in the liquid remain the same as that of the vapor at a specific temperature. Separation of a multi-component azeotropic mixture into pure substances is difficult to achieve by a general distillation method, therefore the elimination of the azeotropic point is required to separate each component in a high purity (Lee J. W. et al., Ind. Eng. Chem. Res., 39(4), 1061-1063 (2000)).

Pressure-swing distillation (PSD), one of the distillation processes to eliminate the azeotropic point, is a method of adjusting the azeotropic point using two distillation columns with different pressures, in which, based on the fact that the composition of the azeotropic mixture changes depending on the pressure, (J. Knapp et al., Ind. Eng. Chem. Res., 31(1), 346-357 (1992); H. Lee et al., Appl. Therm. Eng., 195, 117198 (2021)). For not only a two-component mixture but also a multi-component mixture, when the azeotropic point changes significantly as the pressure varies, separation may be achieved using an additional distillation column (T. Shi et al., Sep. Purif. Technol., 238, 116416 (2020)).

The target product of the present invention, dimethyl carbonate, is produced together with ethylene glycol through the transesterification reaction of ethylene carbonate. A conventional production process consists of a three-distillation column apparatus in which ethylene glycol is produced through a reactive distillation column and discharged through the bottom outlet, and an azeotropic mixture of dimethyl carbonate and methanol, which is discharged through the top outlet, is separated into pure substances by pressure-swing distillation (S. J. Wang et al., Comput. Chem. Eng., 34(3), 361-373 (2010)).

However, in the case of pressure-swing distillation, additional energy is consumed in the process of varying pressure, and operating costs increase due to the fact that the operation of two distillation columns is forced. Accordingly, various types of heat integration processes have been proposed as an alternative to processes with high operating costs and energy consumption, but most of these processes use internal heat integration based on the temperature difference between the rectifying section and the stripping section of a single distillation column, or external heat integration based on a compressor or direct heat exchange using a heat exchanger. In addition, there are few new processes that utilize multiple heat integration methods simultaneously, even though additional heat integration is possible. Regarding a three-distillation column process for production of dimethyl carbonate, a study on an enhanced process using only external heat integration has been conducted (Z. Huang et al., Ind. Eng. Chem. Res., 53(8), 3321-3328 (2014)).

Therefore, there is a demand for an improved three-distillation column process for production of dimethyl carbonate that overcomes the above-described problems.

Accordingly, the present inventors have made extensive efforts to develop an improved distillation process, and as a result, have found that in a dimethyl carbonate production process, when internal and external heat integration is simultaneously applied between a high-pressure distillation column and a low-pressure distillation column, and in addition, when a vapor recompression heat pump configured to compress and heat a fluid and transfer the heat to a fluid having a relatively low temperature is applied together to achieve additional heat exchange with a reactive distillation column, it is possible to improve the process in terms of energy and economic efficiency by reducing energy consumption while reducing investment and operating costs of a reboiler and a condenser, which are required in a conventional process, thereby completing the present invention.

PRIOR ART DOCUMENTS

Patent Documents (Patent Document 1) Korean Patent Application Publication No. 10-2019-0089192
(Patent Document 2) Korean Patent Application Publication No. 10-2020-0096981

SUMMARY OF THE INVENTION

The present invention has been made in view of the above-described problems, and it is an object of the present invention to provide a process of maximizing thermal efficiency and energy efficiency through a combination of units by introducing internal and external heat integration between distillation columns and additional units such as a vapor recompression heat pump to the three-distillation column process for producing dimethyl carbonate.

To achieve the above object, the present invention provides a distillation apparatus for production of dimethyl carbonate comprising: (a) an internal heat integration method having a double annular distillation column structure, which is provided by overlapping high-pressure and low-pressure distillation columns to achieve heat transfer between the columns; (b) an external heat integration method comprising an external heat exchanger for direct heat exchange between a gas discharged from the top of the high-pressure distillation column and a liquid discharged from the bottom of the low-pressure distillation column; or (c) a vapor recompression heat pump configured to compress and heat the gas discharged from the top of the reactive distillation column and supply heat to the liquid discharged from the bottom of the low-pressure distillation column, and a method of fractionally distilling an azeotropic mixture using the above apparatus. The present invention also provides a heat integration process that uses both an internal heat integration unit and an external heat integration unit; a hybrid heat integration process that uses both an internal heat integration unit and a vapor recompression heat pump; and a hybrid heat integration process that uses both an external heat integration unit and a vapor recompression heat pump.

DESCRIPTION OF DRAWING SYMBOLS

Figure 1:
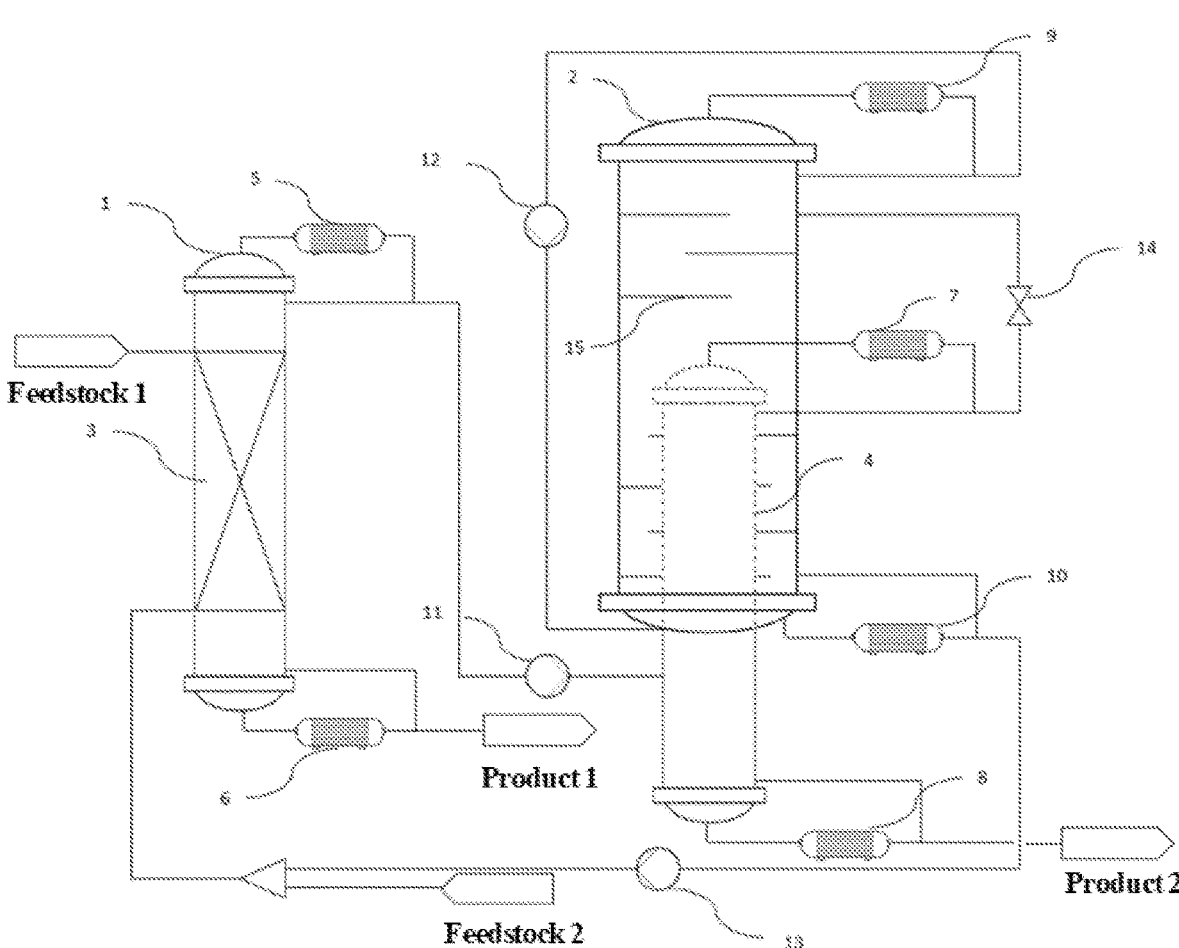
FIG. 1 shows a pressure-swing distillation process for separating a dimethyl carbonate/methanol azeotropic mixture produced in a reactive distillation process in which transesterification of ethylene carbonate occurs, and includes a double annular distillation column structure for internal heat exchange between the partial rectifying section of a high-pressure distillation column and the partial stripping section of a low-pressure distillation column.

1: reactive distillation column
2: low-pressure distillation column
3: reaction stages
4: high-pressure distillation column
5: reactive distillation column condenser
6: reactive distillation column reboiler
7: high-pressure distillation column condenser
8: high-pressure distillation column reboiler
9: low-pressure distillation column condenser
10: low-pressure distillation column reboiler
11, 12: high-pressure distillation column inlet pump
13: reactive distillation column inlet pump
14: control valve
15: low-pressure distillation column tray 16: high pressure-low pressure distillation column heat exchanger
17: vapor recompression heat pump
18: reactive distillation-low pressure distillation column heat exchanger

DETAILED DESCRIPTION OF THE INVENTION

Unless otherwise defined, all technical and scientific terms used in the present specification have the same meanings as commonly understood by those skilled in the art to which the present disclosure pertains. In general, the nomenclature used in the present specification is well known and commonly used in the art.

The present invention presents a hybrid heat integration process including an appropriate combination of internal and external heat integration between pressure-swing distillation columns and a vapor recompression heat pump, which is a unit for increasing thermal efficiency, thereby presenting an enhanced process improved in terms of energy and economic efficiency compared to a conventional three-distillation column apparatus. It has been confirmed that thermal efficiency is increased by transferring the heat from the overhead vapor stream to the reboiler of the distillation column, therefore the operating cost of the reboiler or condenser can be reduced. In addition, it has been confirmed that the effect of saving energy and reducing investment cost are obtained by increasing the temperature of the gas through a vapor recompression heat pump so as to enable heat exchange with another fluid requiring heat.

Therefore, the present invention is directed to a hybrid heat integration of three-distillation column apparatus for production of dimethyl carbonate including: an internal heat integration method having a double annular distillation column structure, which is provided by overlapping high-pressure and low-pressure distillation columns to achieve heat transfer between the columns; an external heat integration method comprising an external heat exchanger for heat exchange between a gas discharged from the top of the high-pressure distillation column and a liquid discharged from the bottom of the low-pressure distillation column; or a vapor recompression heat pump that enables heat exchange with the liquid discharged from the bottom of the low-pressure distillation column by increasing the temperature of the gas discharged from the top of the reactive distillation column.

The present invention is also directed to a hybrid heat integration method comprising using internal and external heat between a high-pressure distillation column and a low-pressure distillation column, and a vapor recompression heat pump for increasing thermal efficiency, in order to maximize the energy efficiency of a dimethyl carbonate production process consisting of a reactive distillation and the pressure swing distillation columns.

The present invention is directed to a distillation apparatus for production of dimethyl carbonate comprising: a reactive distillation column 1; a reactive distillation column reboiler 6; a reactive distillation column condenser 5; and pressure-swing distillation columns, wherein the reactive distillation column 1 comprises a reaction stages 3 in which a reaction that produces an azeotropic mixture containing ethylene glycol and dimethyl carbonate from ethylene carbonate and methanol by transesterification occurs. The reactive distillation column reboiler 6 connected to the reactive distillation column 1 discharges ethylene glycol as a liquid phase, the reactive distillation column condenser 5 connected to the reactive distillation column 1 liquefies the azeotropic mixture. The pressure-swing distillation columns include a high-pressure distillation column 4 and a low-pressure distillation column 2, wherein the high-pressure distillation column 4 separates dimethyl carbonate in a liquid state from the azeotropic mixture liquefied in the reactive distillation column condenser 5, and the low-pressure distillation column 2 separates methanol in a liquid state from the azeotropic mixture liquefied in a high-pressure distillation column condenser 7 connected to the top of the high-pressure distillation column 4.

In the present invention, the pressure-swing distillation columns may have a double annular distillation column structure for internal heat integration.

In the present invention, internal heat integration means a double annular distillation column structure for heat exchange between the partial rectifying section of the high-pressure distillation column and the partial stripping section of the low-pressure distillation column with respect to the pressure-swing distillation columns composed of the high-pressure and low-pressure distillation columns. The double annular distillation column structure may be provided by overlapping the upper portion of the high-pressure distillation column 4 with the lower portion of the low-pressure distillation column 2 to achieve heat exchange therebetween.

In one embodiment of the present invention, 10 stages of the high-pressure distillation column, excluding the condenser stage, and 10 stages of the low-pressure distillation column, excluding the reboiler stage, are overlapped with one another. The amount of heat exchanged is obtained based on the overall heat transfer coefficient (U) calculated in consideration of flow rate, temperature, and pressure conditions in an environment provided with a double annular column structure, through the computational fluid dynamics simulation.

In the present invention, the apparatus may further comprise a high pressure-low pressure distillation column heat exchanger 16.

In the present invention, the external heat integration method comprising the high pressure-low pressure distillation column heat exchanger 16 refers to a structure that uses a heat exchanger so that direct heat exchange occurs between gas discharged from the top of the high-pressure distillation column and liquid discharged from the bottom of the low-pressure distillation column. Here, the external heat integration method may be configured to vaporize all of the liquid from the low-pressure distillation column using the latent heat of the gas from the high-pressure distillation column or to liquefy all of the gas from the high-pressure distillation column using the latent heat of the liquid from the low-pressure distillation column, in order to increase thermal efficiency.

In one embodiment of the present invention, the high pressure-low pressure distillation column heat exchanger 16 may be connected to the top of the high-pressure distillation column 4 and the bottom of the low-pressure distillation column 2, and allows direct heat exchange between the gas discharged from the top of the high-pressure distillation column and the liquid discharged from the bottom of the low-pressure distillation column. It could be confirmed that the heat of the fluid with high latent heat among the fluids introduced into the heat exchanger 16 replaced the role of the heat required for the reboiler/condenser on the side with low latent heat, thereby achieving a large energy saving.

In the present invention, the apparatus may further comprise a vapor recompression heat pump 17. The vapor recompression heat pump is used for heat exchange between the reactive distillation column and the pressure-swing distillation columns, and is configured to compress the gas from the top of the reactive distillation column and transfer the heat to another fluid.

In the present invention, the vapor recompression heat pump 17 may be connected to the top outlet of the reactive distillation column 1 and configured to compress and heat the overhead gas so that the fluid may exchange heat with the liquid discharged from the bottom of the low-pressure distillation column 2.

In the present invention, the apparatus may further comprise a reactive distillation-low pressure distillation column heat exchanger 18.

In one embodiment of the present invention, it could be confirmed that, when the temperature of the fluid was raised through the vapor recompression heat pump 17 and then the fluid was heat-exchanged through the heat exchanger 18, the heat of the fluid with high latent heat replaced the role of the heat required for the reboiler/condenser on the side with low latent heat, thereby achieving large energy saving.

In the present invention, hybrid heat integration refers to an enhanced process improved in terms of energy and economic efficiency compared to existing processes by the simultaneous use of the above-described internal or external heat integration and the vapor recompression heat pump. The present invention proposes three hybrid heat integration processes.

In the present invention, hybrid heat integration by the simultaneous use of internal heat integration and external heat integration can reduce the operating cost of the condenser of the high-pressure distillation column or the reboiler of the low-pressure distillation column through (a) internal heat integration that enables heat exchange between distillation column stages through modification into a double annular distillation column structure of the high-pressure and low-pressure distillation, and (b) external heat integration including direct heat exchange between the gas from the top of the high-pressure distillation column and the liquid from the bottom of the low-pressure distillation column.

In the present invention, hybrid heat integration by the simultaneous use of internal heat integration and the vapor recompression heat pump presents an enhanced process improved in terms of energy and economy efficiency through the simultaneous use of (a) internal heat integration that enables heat exchange between distillation column stages through modification into a double annular distillation column structure of the high-pressure and low-pressure distillation columns, and (b) the vapor recompression heat pump configured to compress the gas from the top of the reactive distillation column, therefore the temperature of the gas increases and transfer the heat thereof to another fluid.

In the present invention, hybrid heat integration by the simultaneous use of external heat integration and the vapor recompression heat pump presents an enhanced process improved in terms of energy and economy efficiency through the simultaneous use of (a) a heat exchanger that performs direct heat exchange between the gas discharged from the top of the high-pressure distillation column of the pressure-swing column and the liquid discharged from the bottom of the low-pressure distillation column, and (b) the vapor recompression heat pump configured to compress the overhead vapor from the top of the reactive distillation column to high pressure to increase the temperature of the gas and transfer the heat thereof to another fluid.

Therefore, in another aspect, the present invention is directed to a method of fractionally distilling an azeotropic mixture containing dimethyl carbonate and methanol by using the pressure swing distillation apparatus for production of dimethyl carbonate.

The method for fractional distillation may comprise steps of: (a) introducing the azeotropic mixture into the high-pressure distillation column 4, passing the azeotropic mixture through the high-pressure distillation column reboiler 8, and discharging 99.5% pure dimethyl carbonate through the bottom outlet; (b) heating the top of the high-pressure distillation column 4, and then introducing the azeotropic mixture liquefied in the high-pressure distillation column condenser 7 into the low-pressure distillation column 2; (c) heating the top of the low-pressure distillation column 2, and then discharging the azeotropic mixture liquefied in the low-pressure distillation column condenser 9; (d) passing through the bottom of the low-pressure distillation column 2 and the low-pressure distillation column reboiler 10, discharging 99.9% pure methanol through the bottom outlet; and (e) allowing the heat generated in step (b) to transfer heat to the gas and liquid at the bottom of the low-pressure distillation column 2 through the double annular structure.

In the present invention, the method for fractional distillation may comprise steps of: (f) recycling the azeotropic mixture of step (c) to the high-pressure distillation column 4 of step (a) by a high-pressure distillation column feeding pump 12; and (g) recycling the liquid, discharged through the bottom outlet of the low-pressure distillation column 2 in step (d), to the reactive distillation column 1.

In the present invention, the method for fractional distillation may further comprise a step of performing direct heat exchange between the gas discharged from the top of the high-pressure distillation column 4 and the liquid discharged from the bottom of the low pressure distillation column 2, by using the high pressure-low pressure distillation column heat exchanger 16 connected to the top of the high pressure distillation column 4 and the bottom of the low pressure distillation column 2.

In the present invention, the method for fractional distillation may further comprise a step of compressing and heating a fluid by the vapor recompression heat pump 17 connected to the top outlet of the reactive distillation column 1, and heat-exchanging the fluid with the liquid discharged from the bottom of the low-pressure distillation column 2.

In the present invention, the method for fractional distillation further comprises a step of performing direct heat exchange between the gas discharged from the top of the reactive distillation column 1 and the liquid discharged from the bottom of the low-pressure distillation column 2, by using a reactive distillation column-low pressure distillation column heat exchanger 18.

In the present invention, the method for fractional distillation is characterized by using the distillation apparatus for production of dimethyl carbonate, and thus the description of contents overlapping with those described with respect to the distillation apparatus will be omitted.

Hereinafter, the present invention will be described in more detail with reference to examples. These examples are only for illustrating the present invention, and it will be apparent to those skilled in the art that the scope of the present invention is not to be construed as being limited by these examples.

EXAMPLES

The following Examples 1 to 6 were performed by computational process simulation using Aspen Plus™ and ANSYS Fluent.

Example 1: Conventional Dimethyl Carbonate Production Process (Using Reactive Distillation and Pressure-Swing Distillation)

A reactive distillation column in which a reaction that produces dimethyl carbonate and ethylene glycol by the reaction of ethylene carbonate with methanol occurs was firstly designed. 25 kmol/h of ethylene carbonate (boiling point: 248° C.) and 50 kmol/h of methanol (boiling point: 64.535° C.) were supplied to stage 5 and stage 43, respectively. The reactive distillation column had a total of 45 stages, the reflux ratio was 1.4, the condenser pressure was 1 atm, and the condenser temperature was 63.82° C. At the bottom outlet, 99.5 mol % pure ethylene glycol was produced at a flow rate of 25.045 kmol. 159.475 kmol/h of a methanol/dimethyl carbonate mixture containing 84.3 mol % of methanol was discharged through the top outlet, compressed to 10 atm by a pump, and then supplied to stage 16 of a high-pressure distillation column for pressure-swing distillation. The high-pressure distillation column consisted of 23 stages, the reflux ratio was 1.2, and the condenser pressure was 10 atm. In the high-pressure distillation column, dimethyl carbonate with a purity of 99.5 mol % was produced at a flow rate of 25.044 kmol/h through the bottom outlet due to the difference in boiling point. A methanol/dimethyl carbonate azeotropic mixture containing 93.4 mol % of methanol was discharged through the top outlet of the high-pressure distillation column at a flow rate of 316.297 kmol/h, and condensed by the condenser of the high-pressure distillation column and was introduced into stage 10 of a low-pressure distillation column. The low-pressure distillation column was composed of 35 stages, the reflux ratio was 3.1, and the condenser pressure was 1 atm. In the low-pressure distillation column, methanol with a purity of 99.9 mol % was discharged through the bottom outlet at a flow rate of 134.432 kmol/h and recycled to the methanol inlet of the reactive distillation column. A methanol/dimethyl carbonate azeotropic mixture containing 88.8 mol % dimethyl carbonate was discharged through the top outlet of the low-pressure distillation column at 181.886 kmol/h and recycled to stage 12 of the high-pressure distillation column to further increase the conversion rate.

Example 2: Enhanced Process Including Internal Heat Integration Between Pressure-Swing Distillation Columns The process of Example 2 was carried out in the same manner as in Example 1, except that internal heat integration between the pressure swing distillation columns was performed in the process of Example 1. A double annular distillation column structure was constructed using ANSYS Fluent, a computational fluid dynamics simulation tool (FIG. 1), and the amount of the heat exchanged from the upper portion of the inner high-pressure distillation column (stages 2 to 11) to the lower portion of the outer low-pressure distillation column (stages 25 to 34) was calculated for each stage. This included a process of calculating an overall heat transfer coefficient (U) in consideration of temperature change. The heat exchange area was calculated as 3.535 m², which is the outer wall area of the high-pressure distillation column, and the overall heat transfer coefficient (U) was calculated as 455.7 W/m²K, which is the average value of the heat transfer coefficients of the heat-exchanged stages. In addition, the amount of heat exchange was calculated based on the 'effective temperature difference' obtained by subtracting 20° C. from the actual temperature difference, assuming the pinch condition that the required minimum temperature difference between stages for effective heat exchange should be more than 20° C.

As in Example 1, through internal heat integration, dimethyl carbonate with a purity of 99.5 mol % was produced at the bottom of the high-pressure distillation column, and methanol with a purity of 99.9 mol % was produced in the low-pressure distillation column and recycled to the methanol inlet of the reactive distillation column.

Table 1 below shows the amount of heat exchange for each stage based on a heat transfer coefficient of 455.7 W/m²K calculated in Example 2.

TABLE 1

| High-pressure distillation column Stage number | Low-pressure distillation column Stage number | Actual temperature difference (K) | Effective temperature difference (K) (Actual temperature difference − 20 K) | Amount of heat exchange (kW) |
|---|---|---|---|---|
| 2 | 25 | 68.9346 | 48.9346 | 78.8269 |
| 3 | 26 | 68.8017 | 48.8017 | 78.6128 |
| 4 | 27 | 68.6725 | 48.6725 | 78.4047 |
| 5 | 28 | 68.5475 | 48.5475 | 78.2034 |
| 6 | 29 | 68.4254 | 48.4254 | 78.0067 |
| 7 | 30 | 68.3077 | 48.3077 | 77.8171 |
| 8 | 31 | 68.1918 | 48.1918 | 77.6304 |
| 9 | 32 | 68.0783 | 48.0783 | 77.4475 |
| 10 | 33 | 67.967 | 47.967 | 77.2682 |
| 11 | 34 | 67.8584 | 47.8584 | 77.0933 |

As a result of heat exchange by applying the amount of heat exchange to Aspen plus simulation, heat (6,558.75 kW) required to condense gas into liquid in the high-pressure distillation column condenser in a conventional process was reduced to 5,942.84 kW in the internal heat integration process. In addition, heat (6,681.3 kW) required to vaporize liquid into gas in the low-pressure distillation column reboiler was reduced to 5,933.37 kW in the internal heat integration process. Energy consumption was decreased by 3.36%, and cost was decreased by 2.64%.

Figure 2:
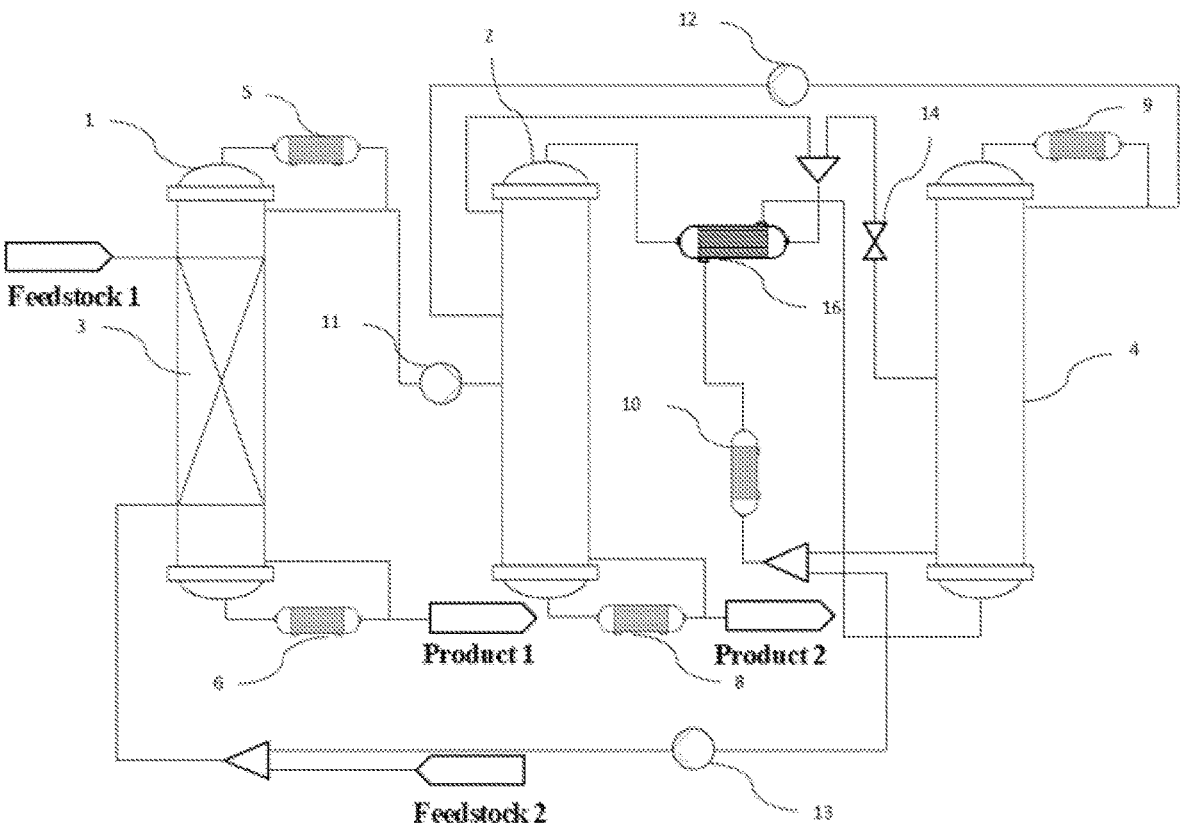
FIG. 2 shows a pressure-swing distillation process for separating a dimethyl carbonate/methanol azeotropic mixture, and includes a heat exchanger for external heat exchange between a gas discharged from the top of a high-pressure distillation column and a liquid discharged from the bottom of a low-pressure distillation column.

Example 3: Enhanced Process Including External Heat Integration Between Pressure-Swing Distillation Columns The process of Example 3 was carried out in the same manner as in Example 1, except that external heat integration between the pressure swing distillation columns was additionally operated from the process of Example 1. Initial conditions were the same as those in Example 1. The gas discharged from the high-pressure distillation column in Example 1 was at 137.26° C. and had a flow rate of 493.486 kmol/h before passing through the condenser, and the liquid discharged from the bottom of the low-pressure distillation column was at 69.989° C. and had a flow rate of 688.526 kmol/h before passing through the reboiler. A heat exchanger was used for direct heat exchange between these two fluids (FIG. 2). Since the latent heat of the liquid discharged from the bottom of the low-pressure distillation column was greater, the design specification of the heat exchanger was set such that the liquid discharged from the bottom of the low-pressure distillation column would liquefy all of the gas discharged from the top of the high-pressure distillation column. The phase of the liquid discharged from the bottom of the low-pressure distillation column slightly changed to 79.7% liquid and 20.3% gas after heat exchange. Then, a heater serving as a reboiler of the low-pressure distillation column was used to change the phase to 100% gas, and the gas was recycled to the low-pressure distillation column.

In this case, the role of the condenser of the high-pressure distillation column was replaced by the liquid discharged from the bottom of the low-pressure distillation column, and thus heat corresponding to the condenser of the high-pressure distillation column was reduced. Heat (6,558.75 kW) required for the condenser of the high-pressure distillation column in the conventional process became 0 kW in the external heat integration process. In addition, the gas discharged from the top of the high-pressure distillation column provided some of the heat for vaporizing the liquid discharged from the bottom of the low-pressure distillation column, and thus the heat required for the reboiler of the low-pressure distillation column was reduced. Heat (6681.3 kW) required for the reboiler of the low-pressure distillation column in the conventional process was reduced to 1,414 kW in the external heat integration process, resulting in a significant reduction in total energy consumption of 33.04% and a cost reduction of 26.97%.

In addition, in the external heat integration process, ethylene glycol, dimethyl carbonate, and methanol having purities of 99.5 mol %, 99.5 mol % and 99.9 mol %, respectively, were produced in the reactive distillation column, high-pressure distillation column, and low-pressure distillation column, respectively, as same as Example 1.

Example 4: Hybrid Heat-Integrated Enhanced Process Using Both Internal and External Heat Integration Between Pressure Swing Distillation Columns An hybrid heat-integrated enhanced process was designed by simultaneously applying the external heat integration method of Example 3 and the internal heat integration method of Example 2.

Figure 3:
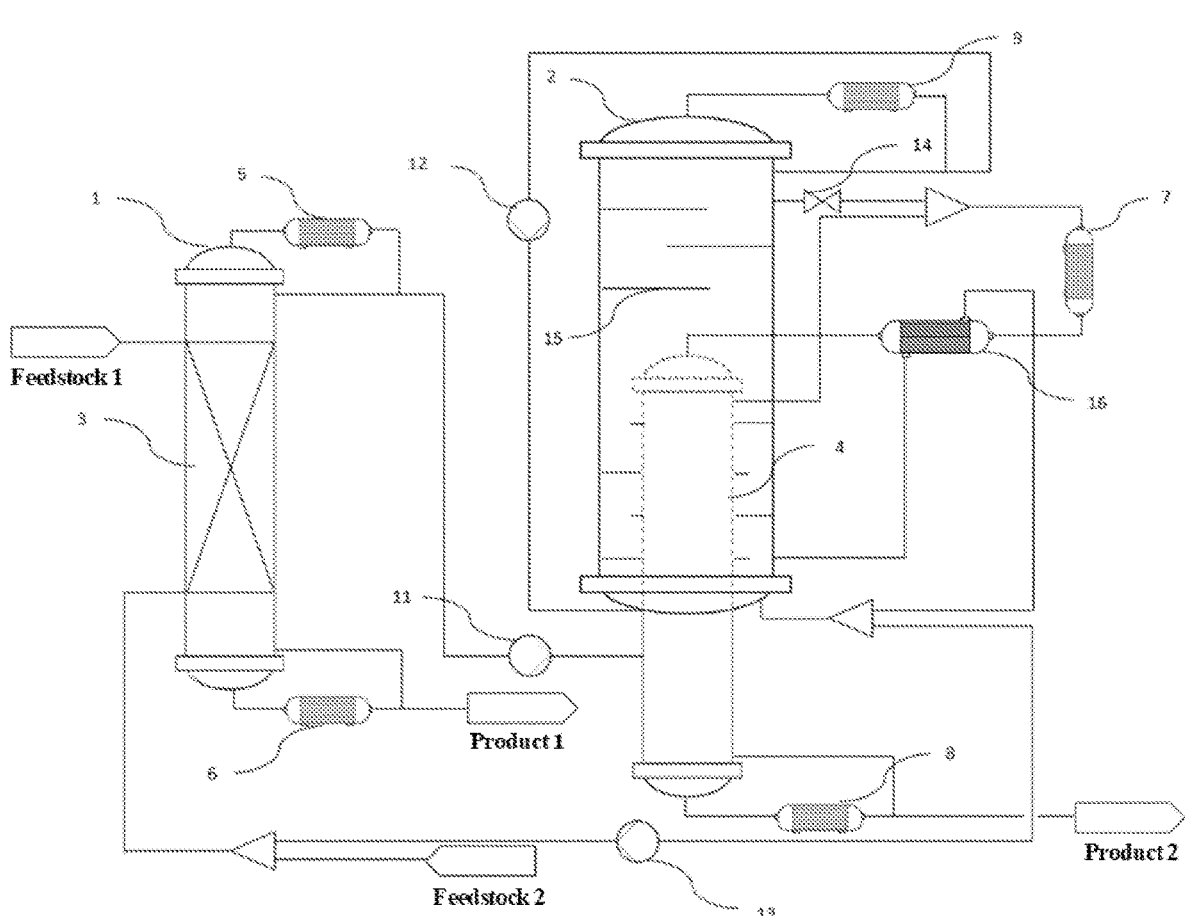
FIG. 3 shows performing both internal and external heat integration for hybrid heat exchange according to the present invention, and includes the double annular distillation column for internal heat integration between the high-pressure distillation column and the low-pressure distillation column, shown in FIG. 1, and the heat exchanger for external heat integration shown in FIG. 2.

As in Example 1, in the reactive distillation column, transesterification of ethylene carbonate occurs. Then, the internal heat integration between the upper portion (stages 1 to 11) of the high-pressure distillation column and the lower portion (stages 25 to 34) of the low-pressure distillation column proceeded, and in addition, direct heat exchange between the gas (stage 1) discharged from the top of the high-pressure distillation column and the liquid (stage 35) discharged from the bottom of the low-pressure distillation column occurred through a heat exchanger (FIG. 3).

It was confirmed that the gas from the top of the high-pressure distillation column in the process of Example 2 was at 137.258° C. and discharged at 417.443 kmol/h before passing through the condenser, and the liquid from the bottom from the low-pressure distillation column was at 69.9885° C. and discharged at 611.442 kmol/hr before passing through the reboiler. In this case, since the latent heat of the gas discharged from the top of the high-pressure distillation column was higher, the design specification of the heat exchanger was set such that the gas discharged from the top would vaporize all of the liquid discharged from the bottom. The gas discharged from the top underwent a phase change to 99.75% liquid and 0.25% gas after heat transfer, and then complete liquefaction was achieved by using a heater serving as a condenser of the high-pressure distillation column for complete phase change.

In this case, the amount of heat required for the reboiler of the low-pressure distillation column became 0 kW, and the high-pressure distillation column also achieved nearly complete liquefaction even if only a small amount of heat was supplied thereto, resulting in a significant decrease in energy consumption and a significant increase in economic efficiency compared to those in the conventional process or the internal heat integration process. In the conventional process, the heat required for the high-pressure distillation column condenser was 6,558.75 kW, whereas, in the hybrid heat integration process using both internal and external heat integration, the heat required was 14.7464 kW, and the heat required for the low-pressure distillation column reboiler was reduced from 6,681.3 kW to 0 kW, resulting in a decrease in total energy consumption of 37.4% and a cost reduction of 30.28%. The cost reduction of 30.28% is the highest reduction rate in terms of economic efficiency among the hybrid heat integration processes proposed in the present invention.

Figure 4:
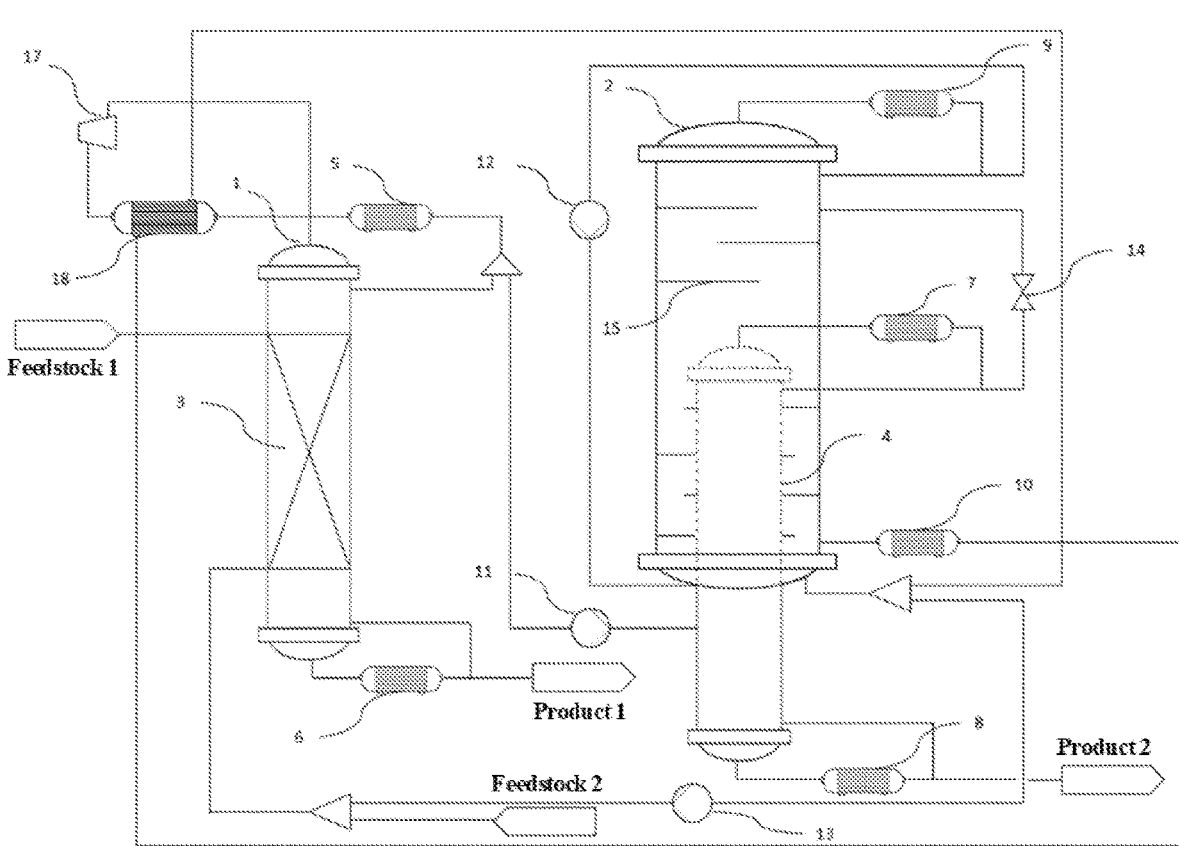
FIG. 4 shows an enhanced distillation process using both internal heat integration and a vapor recompression heat pump for hybrid heat exchange according to the present invention, and includes the double annular distillation column structure for heat exchange between both distillation columns, shown in FIG. 1, and a vapor recompression heat pump configured to increase the temperature of a gas discharged through the top outlet of a reactive distillation column and use the heat for heat exchange.

Example 5: Hybrid Heat-Integrated Enhanced Process Using Internal Heat Integration Between Pressure-Swing Distillation Columns and Vapor Recompression Heat Pump at the Same Time Based on Example 2, a hybrid heat-integrated enhanced process was designed by using internal heat integration and a vapor recompression heat pump at the same time to exchange heat with the reactive distillation column. The vapor recompression heat pump is generally configured to perform heat exchange by compressing and heating one of two fluids having similar temperatures. The temperatures of the gas discharged from the top of the reactive distillation column and the liquid discharged from the bottom of the low-pressure distillation column in Examples 1 and 2 were similar, and thus the gas discharged from the top of the reactive distillation column was introduced to a vapor recompression heat pump (FIG. 4). In this case, the pressure of the heat pump (compressor) was set to 1.32 atm, which is the minimum pressure to meet the minimum temperature of the gas discharged from the top so as to completely vaporize the liquid discharged from the bottom. At this time, the amount of heat required for the vapor recompression heat pump was 97.5817 kW, which is significantly smaller than the amount required for the condenser or reboiler.

The heat required for the condenser of the reactive distillation column was reduced from 3,199.39 kW to 78.8372 kW by this hybrid heat integration. The condenser of the high-pressure distillation column decreased from 6,558.75 kW in the conventional process and 5,942.84 kW in the internal heat integration process to 4,442.72 kW. The heat required for the reboiler of the low-pressure distillation column was reduced from 6,681.3 kW in the conventional process and 5,933.37 kW in internal heat integration to 1,315.03 kW. As a result, the total energy consumption was reduced by 29.41% and the cost by 24.6% compared to those in the conventional process, which resulted in significant energy and cost savings compared to those in the internal heat integration process.

Figure 5:
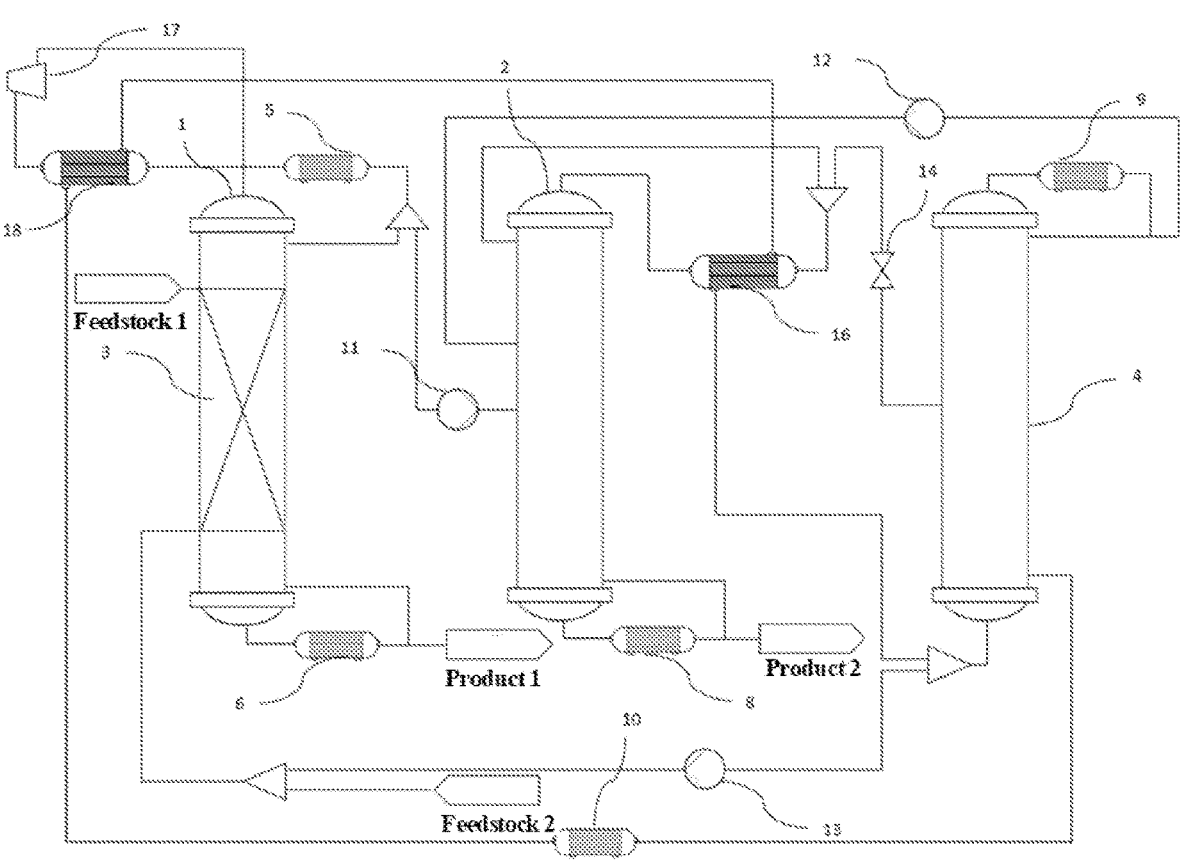
FIG. 5 shows an enhanced distillation process using both external heat integration and a vapor recompression heat pump for hybrid heat exchange according to the present invention, and includes the heat exchanger shown in FIG. 2 and the vapor recompression heat pump shown in FIG. 4.

Example 6: Hybrid Heat-Integrated Enhanced Process Using External Heat Integration Between Pressure Swing Distillation Columns and Vapor Recompression Heat Pump at the Same Time Based on Example 3, a hybrid heat-integrated enhanced process was designed by using external heat integration and a vapor recompression heat pump at the same time to exchange heat with the reactive distillation column (FIG. 5). As in Example 5, heat exchange occurred between the gas discharged from the top of the reactive distillation column and the liquid discharged from the bottom of the low-pressure distillation column. In this case, the pressure of the heat pump (compressor) was set to 1.805 atm, which is the minimum pressure to meet the minimum temperature of the gas discharged from the top so as to completely vaporize the liquid discharged from the bottom. At this time, the amount of heat required for operation of the vapor recompression heat pump was 272.27 kW.

This hybrid heat-integrated enhanced process significantly reduced the amount of heat required for the reactive distillation column condenser, high-pressure distillation column condenser and low-pressure distillation column reboiler. The heat required for the condenser of the reactive distillation column was reduced from 3,199.38 kW in the conventional process to 2,593.06 kW, and the heats required for the high-pressure distillation column condenser and the low-pressure distillation column reboiler were reduced from 6,558.75 kW and 6,681.3 kW, respectively, both to 0 kW, resulting in a reduction in total energy consumption of 38.33% and a cost reduction of 27.91%. The energy consumption reduction rate of 38.33% is the highest reduction rate in terms of energy among the hybrid thermal integration processes proposed in the present invention. Compared to hybrid heat integration using both internal and external heat integration, there was a slight increase in cost due to the investment cost of the vapor recompression heat pump.

According to the present invention, in a process using reactive distillation and pressure-swing distillation, it is possible to reduce the operating cost of a condenser or a reboiler through a combination of internal and external heat integration between pressure-swing distillation columns and a vapor recompression heat pump, an additional unit that increases thermal efficiency. The hybrid heat integration process including internal heat integration is capable of minimizing the site area due to the unification of the units compared to conventional units, and the hybrid heat integration process including external heat integration is capable of significantly reducing investment costs and energy consumption by offsetting the heat required for the condenser or reboiler through direct heat exchange.

Although the present invention has been described in detail with reference to specific features, it will be apparent to those skilled in the art that this description is only of a preferred embodiment thereof, and does not limit the scope of the present invention. Thus, the substantial scope of the present invention will be defined by the appended claims and equivalents thereto.

What is claimed is:

1. A distillation apparatus for preparing dimethyl carbonate comprising: a reactive distillation column; a reactive distillation column reboiler; a reactive distillation column condenser; and pressure-swing distillation columns,
   wherein:
   the reactive distillation column comprises reaction stages in which a reaction that produces ethylene glycol and an azeotropic mixture containing methanol and dimethyl carbonate from transesterification of ethylene carbonate occurs;
   the reactive distillation column reboiler connected to the reactive distillation column discharges the ethylene glycol as a liquid;

the reactive distillation column condenser connected to the reactive distillation column liquefies the azeotropic mixture, and the pressure-swing distillation columns include a high-pressure distillation column and a low-pressure distillation column, wherein the high-pressure distillation column separates dimethyl carbonate in a liquid state from the azeotropic mixture liquefied in the reactive distillation column condenser, the low-pressure distillation column separates methanol in a liquid state from the azeotropic mixture liquefied in a high-pressure distillation column condenser connected to a top of the high-pressure distillation column, and the pressure-swing distillation columns have a double annular distillation column structure for internal heat integration.

2. The distillation apparatus for preparing dimethyl carbonate of claim 1, wherein the double annular distillation column structure is provided by overlapping a partial rectifying section of the high-pressure distillation column with a partial stripping section of the low-pressure distillation column to achieve heat exchange therebetween.

3. The distillation apparatus for preparing dimethyl carbonate of claim 1, further comprising a high pressure-low pressure distillation column heat exchanger.

4. The distillation apparatus for preparing dimethyl carbonate of claim 3, wherein the high pressure-low pressure distillation column heat exchanger is connected to the top of the high-pressure distillation column and a bottom of the low-pressure distillation column, and allows direct heat exchange between the gas discharged from the top of the high-pressure distillation column and the liquid discharged from the bottom of the low-pressure distillation column.

5. The distillation apparatus for preparing dimethyl carbonate of claim 1 or claim 3, further comprising a vapor recompression heat pump.

6. The distillation apparatus for preparing dimethyl carbonate of claim 5, wherein the vapor recompression heat pump is connected to a top outlet of the reactive distillation column and configured to compress and heat a fluid so that the fluid exchanges heat with the liquid discharged from the bottom of the low-pressure distillation column.

7. The distillation apparatus for preparing dimethyl carbonate of claim 5, further comprising a reactive distillation-low pressure distillation column heat exchanger.

8. The distillation apparatus for preparing dimethyl carbonate of claim 7, wherein the reactive distillation-low pressure distillation column heat exchanger allows direct heat exchange between the gas discharged from the top of the reactive distillation column and the liquid discharged from the bottom of the low-pressure distillation column.

9. A method of fractionally distilling an azeotropic mixture containing dimethyl carbonate and methanol, in the distillation apparatus for production of dimethyl carbonate of claim 1, the method comprising introducing ethylene carbonate and methanol to the reactive distillation column, and transesterifying the ethylene carbonate in the reactive distillation column to produce ethylene glycol and the azeotropic mixture containing dimethyl carbonate and methanol.

10. The method of claim 9, comprising:

(a) introducing the azeotropic mixture into the high-pressure distillation column, passing the azeotropic mixture through the high-pressure distillation column reboiler, and discharging 99.5% pure dimethyl carbonate through a bottom outlet;

(b) heating a top of the high-pressure distillation column, and then introducing the azeotropic mixture liquefied in the high-pressure distillation column condenser into the low-pressure distillation column;

(c) heating the top of the low-pressure distillation column, and then discharging the azeotropic mixture liquefied in the low-pressure distillation column condenser;

(d) passing the azeotropic mixture through the bottom of the low-pressure distillation column and the low-pressure distillation column reboiler and discharging 99.9% pure methanol through a bottom outlet of the low-pressure distillation column; and (e) allowing the heat generated in step (b) to heat the gas and liquid at the bottom of the low-pressure distillation column through the double annular structure and transferring the heat.

11. The method of claim 10, further comprising:

(f) recycling the azeotropic mixture of step (c) to the high-pressure distillation column of step (a) by a high-pressure distillation column feeding pump; and (g) recycling the liquid, discharged through the bottom outlet of the low-pressure distillation column in step (d), to the reactive distillation column.

12. The method of claim 9, further comprising performing direct heat exchange between the gas discharged from the top of the high-pressure distillation column and the liquid discharged from the bottom of the low-pressure distillation column, by using the high pressure-low pressure distillation column heat exchanger connected to the top of the high-pressure distillation column and the bottom of the low-pressure distillation column.

13. The method of claim 10 or claim 12, further comprising compressing and heating a fluid by the vapor recompression heat pump connected to a top outlet of the reactive distillation column, and heat-exchanging the fluid with the liquid discharged from the bottom of the low-pressure distillation column.

14. The method of claim 13, further comprising performing direct heat exchange between the gas discharged from the top of the reactive distillation column and the liquid discharged from the bottom of the low-pressure distillation column, by using a reactive distillation column-low pressure distillation column heat exchanger.

* * * * *